United States Patent
Husar et al.

(10) Patent No.: US 10,451,615 B2
(45) Date of Patent: Oct. 22, 2019

(54) METHODS AND DEVICES FOR PERFORMING HIGH DYNAMIC RANGE IMMUNOASSAYS

(71) Applicant: MBIO DIAGNOSTICS, INC., Boulder, CO (US)

(72) Inventors: Gregory M. Husar, Longmont, CO (US); Sarah Rachel Bickman, Boulder, CO (US); Michael J. Lochhead, Boulder, CO (US)

(73) Assignee: MBio Diagnostics, Inc., Boulder, CO (US)

( * ) Notice: Subject to any disclaimer, the term of this patent is extended or adjusted under 35 U.S.C. 154(b) by 534 days.

(21) Appl. No.: 14/959,699

(22) Filed: Dec. 4, 2015

(65) Prior Publication Data

US 2016/0161474 A1    Jun. 9, 2016

Related U.S. Application Data

(60) Provisional application No. 62/088,124, filed on Dec. 5, 2014.

(51) Int. Cl.
*G01N 33/536* (2006.01)
*G01N 33/543* (2006.01)

(52) U.S. Cl.
CPC . *G01N 33/54306* (2013.01); *G01N 33/54366* (2013.01)

(58) Field of Classification Search
None
See application file for complete search history.

(56) References Cited

U.S. PATENT DOCUMENTS

| 4,140,753 | A | * | 2/1979 | Edgington | ....... G01N 33/57446 436/542 |
| 5,089,391 | A | | 2/1992 | Buechler et al. | |
| 6,689,565 | B2 | * | 2/2004 | Nikiforov | ................ C12Q 1/37 435/6.1 |
| 7,858,321 | B2 | | 12/2010 | Glezer et al. | |
| 2007/0111262 | A1 | | 5/2007 | Li et al. | |
| 2011/0105354 | A1 | | 5/2011 | Glezer et al. | |

(Continued)

FOREIGN PATENT DOCUMENTS

| EP | 1361435 A1 | 11/2003 |
| WO | WO 2001063284 A2 | 8/2001 |

(Continued)

OTHER PUBLICATIONS

International Search Report and Written Opinion corresponding to International Patent Application No. PCT/US2015/063990, dated Feb. 23, 2016, 10 pages.

*Primary Examiner* — Christopher L Chin
(74) *Attorney, Agent, or Firm* — Lathrop Gage LLP

(57) ABSTRACT

A method for performing a high dynamic range immunoassay includes (a) measuring a first signal from a sandwich immunoassay to detect a target analyte in a fluidic sample in a fluidic channel and a second signal from a competitive immunoassay associated with the target analyte in the same fluidic sample in the fluidic channel, and (b) determining ratio of the first signal to the second signal to provide a measure of concentration of the target analyte in the fluidic sample, wherein the measure is applicable to a high dynamic range of concentrations of the target analyte.

9 Claims, 8 Drawing Sheets

(56) References Cited

U.S. PATENT DOCUMENTS

2014/0120556 A1    5/2014  Moll et al.
2014/0186972 A1    7/2014  Campbell et al.
2014/0308661 A1   10/2014  Holmes et al.
2016/0018394 A1*   1/2016  Danielson ............ G01N 33/558
                                                           506/9

FOREIGN PATENT DOCUMENTS

WO    WO 2003/023360 A2    3/2003
WO    WO 2014106033 A1     7/2014

* cited by examiner

METHODS AND DEVICES FOR PERFORMING HIGH DYNAMIC RANGE IMMUNOASSAYS

CROSS-REFERENCE TO RELATED APPLICATIONS

The present application claims the benefit of priority from U.S. Provisional Application Ser. No. 62/088,124 filed Dec. 5, 2014, which is incorporated herein by reference in its entirety.

BACKGROUND

Heterogeneous immunoassays such as enzyme-linked immunosorbent assays (ELISA), bead based immunoassays, and protein microarrays are widely used in the biological sciences and medical diagnostic applications. Immunoassays can be sandwich assays, with specific capture antibodies immobilized on a solid support and a specific detection antibody forming a "sandwich" with the target analyte. The detection antibody may be labeled with a detectable label for signal transduction, such as an enzyme, fluorescent dye, fluorescent particle, etc. The detection antibody may also be labeled using an anti-species antibody conjugated with a detectable label. Various permutations of heterogeneous immunoassays such as competitive and indirect immunoassays are also well known in the art.

Quantitative immunoassays generate data that are typically presented as signal intensity versus concentration, and typically have a sigmoidal shape. The flattening of signal at high analyte concentration can result from saturation of available binding sides on the solid surface. A decrease in signal at very high and increasing target analyte concentration is called the hook effect or prozone effect, and is well-described in the literature. In this case, an excess of analyte depletes available detection reagent (e.g., detection antibody) and therefore decreases signal (see FIG. 2). This paradoxical decrease in signal with increasing target concentration is a problem that must be addressed in immunoassay with large dynamic range.

The most common method for dealing with hook effect is to dilute the sample. In many applications, however, the addition of manual or automated sample processing steps is undesirable, particularly for cost and complexity reasons. Minimizing the number and complexity of steps that a user must perform to execute the test will decrease the cost of the test and also improve the results since there will be fewer opportunities for user error. Although methods that characterize the hook effect exist and some of these methods correct for this effect, to date no method has been developed, which combines hook detection and correction in a single, simple measurement.

Multiple methods that provide hook effect detection have been described. In European Patent Application EP 1 361 435 A1, hook effect is detected by the signal from a specific binding substance and a sandwich reaction, and the device automatically performs a sample dilution. In US Patent Application 2003023360 A2, hook effect is detected by performing a sandwich reaction and a competitive assay for the same analyte, and then a manual dilution step must be performed. Another method of reducing the hook effect is to reduce the analyte concentration by adding a ligand compliment such as is described in U.S. Pat. No. 5,089,391 A. The ligand compliment must be removed before performing the immunoassay, which adds an additional assay step. A different approach uses flow cytometry to detect the analyte concentration on a particle such as a bead to measure the hook effect as described in WO 2001063284 A2.

WO 2014106033 A1 describes a multiple sensor device in which two different concentrations of the same immunosensor are used to detect the analyte concentration. An automated processor determines whether the hook effect is present by either comparing the signal sizes from these two immunoassays or by taking the ratio of the signal sizes. The method disclosed in WO 2014106033 A1 thus requires performing two immunoassays. However, this method does not actually correct for the hook effect, it simply detects the presence of the effect.

U.S. Pat. No. 7,858,321 B2 measures the hook effect by performing immunoassays simultaneously in a multiple well plate with multiple domains per well. Two different immunoassays are simultaneously measured: a sandwich immunoassay and a competitive assay for the analyte. As is the case for WO 2014106033 A1, the method of U.S. Pat. No. 7,858,321 B2 does not correct for the hook effect.

SUMMARY

In an embodiment, a method for performing a high dynamic range immunoassay includes measuring (a) a first signal from a sandwich immunoassay to detect a target analyte in a fluidic sample in a fluidic channel and (b) a second signal from a competitive immunoassay associated with the target analyte in the same fluidic sample in the fluidic channel. The method further includes determining the ratio of the first signal to the second signal to provide a measure of concentration of the target analyte in the fluidic sample, wherein the measure is applicable to a high dynamic range of concentrations of the target analyte.

In an embodiment, a device for performing an assay on a sample includes a capillary channel for containing the sample and a microarray immobilized to a surface of the capillary channel. The microarray includes (a) a first spot including a first capture molecule for specifically binding to a target analyte in the sample to perform a sandwich immunoassay involving the first capture molecule, the target analyte, and a detect reagent added to the sample, and (b) a second spot including a second capture molecule for specifically binding to the detect reagent to perform a competitive assay with the detect reagent to measure amount of detect reagent available to the sandwich immunoassay. The sandwich immunoassay and the competitive assay cooperate to provide a measure of concentration of the target analyte applicable to a high dynamic range of concentrations of the target analyte.

BRIEF DESCRIPTION OF THE DRAWINGS

FIG. 11 illustrates an exemplary high dynamic range immunoassay used to measure the concentration of Ebola VP40 antigen.

FIG. 12 shows layout and an exemplary fluorescence image of a microarray used in the Ebola high dynamic range immunoassay of FIG. 11.

FIG. 13 shows an exemplary standard curve of a sandwich immunoassay obtained in the Ebola high dynamic range immunoassay of FIG. 11.

FIG. 14 shows the standard curve of FIG. 13 together with a standard curve for a competitive immunoassay obtained in the Ebola high dynamic range immunoassay of FIG. 11.

FIG. 15 shows exemplary ratios of the sandwich immunoassay measurements to the competitive immunoassay measurements obtained in the Ebola high dynamic range immunoassay of FIG. 11.

DETAILED DESCRIPTION OF THE EMBODIMENTS

Figure 1:
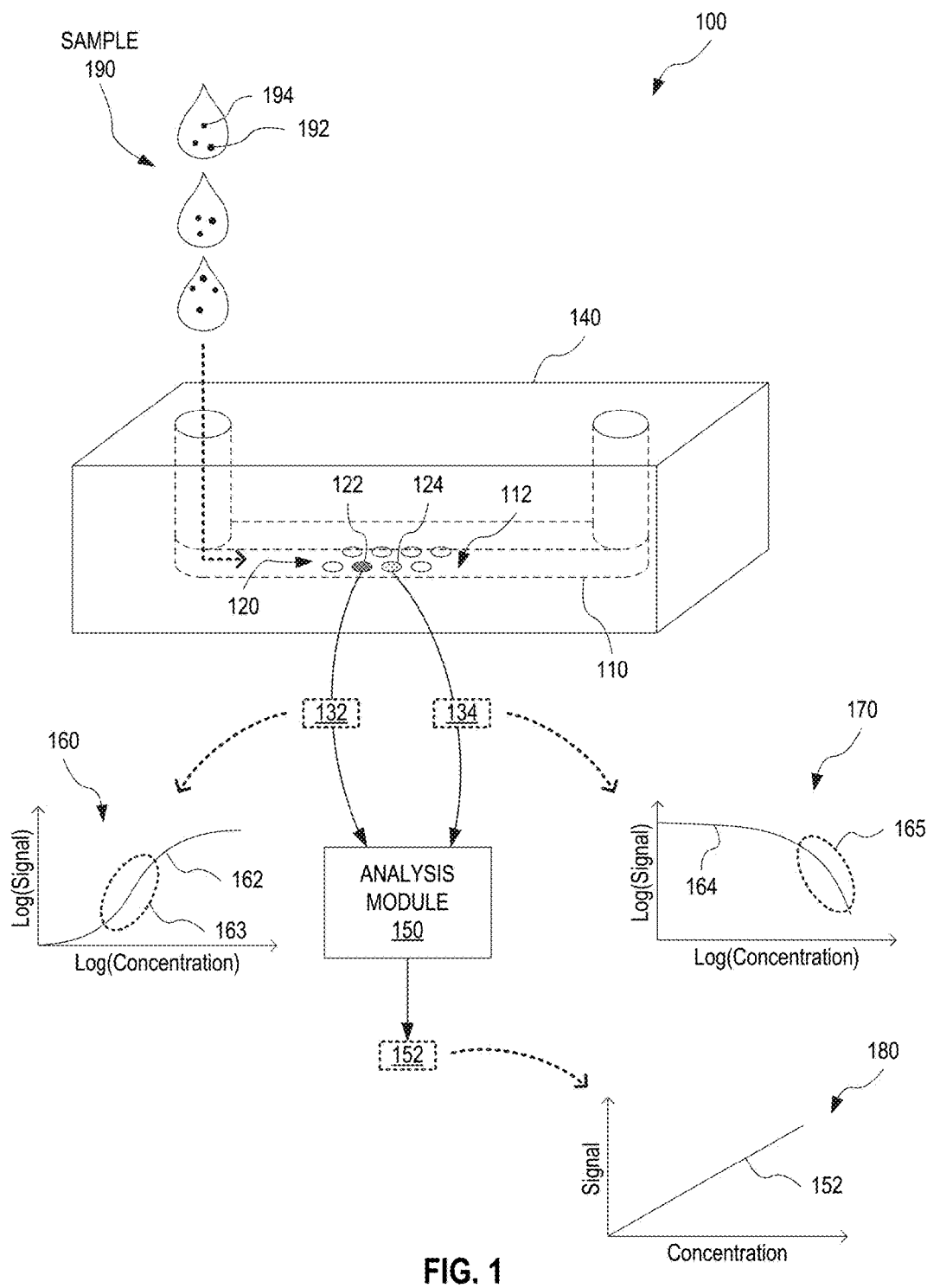
FIG. 1 illustrates a system for performing high dynamic range immunoassays, according to an embodiment.

FIG. 1 illustrates one exemplary system 100 for performing high dynamic range immunoassays. System 100 has integrated hook effect correction and provides a quantitative measurement of the concentration of a target analyte 192 over a high dynamic range. A user needs only deposit a single sample 190, suspected to possibly contain target analyte 192, in a single fluidic channel 110. Thus, system 100 does not require any additional user operations to correct for the hook effect.

System 100 includes an assay device 140 and an analysis module 150. Assay device 140 processes a sample 190 possibly containing target analyte 192. Analysis module 150 makes measurements on assay device 140 and processes these measurements to determine a measure 152 of the concentration of target analyte 192 in sample 190. The processing performed by analysis module 150 includes correcting for the hook effect such that concentration measure 152 is accurate over a high dynamic range. In one example of use, concentration measure 152 is an absolute measure of the concentration of target analyte 192, for example the concentration of target analyte 192 indicated in units of nanograms/milliliters. In another example of use, concentration measure 152 is a relative measure of the concentration of target analyte 192.

Sample 190 may be any liquid substance. Examples of types of sample 190 include, but are not limited to whole blood, blood plasma, blood serum, saliva, urine, lacrimal fluid, spinal fluid and secretion from papillae, food products such as milk, or a sample that is prepared by suspending or dissolving a solid substance or a gel substance into a liquid such as a buffer solution.

Assay device 140 includes fluidic channel 110 and a microarray 120 located within fluidic channel 110. In one embodiment, fluidic channel 110 is an open fluidic channel and microarray 120 is deposited on a surface 112 of fluidic channel 110. For example, fluidic channel 110 may be a capillary channel. In another embodiment, fluidic channel 110 is a porous material, such as a lateral flow strip, and microarray 120 is deposited in and/or on this porous material. In yet another embodiment, fluidic channel 110 has solid, non-porous walls but at least a section of the fluidic channel is filled with a porous material that includes microarray 120. In a further embodiment, fluidic channel includes at least one section that is an open fluidic channel and at least one section that is a porous material. In this embodiment, microarray 120 may be deposited in the open section or in the porous material.

Microarray 120 includes at least two spots: a sandwich immunoassay spot 122 and a competitive immunoassay spot 124. Sandwich immunoassay spot 122 is configured to perform a sandwich immunoassay with target analyte 192 and a detect reagent 194 added to sample 190. Competitive immunoassay spot 124 is configured to perform a competitive assay with detect reagent 194, wherein this competitive assay is influenced by target analyte 192. Microarray 120 may include additional spots and may also include replicates of either or both of sandwich immunoassay spot 122 and competitive immunoassay spot 124.

Herein, a "sandwich immunoassay" refers to an assay wherein a target analyte is bound between an immobilized capture molecule and a detect reagent. Also herein, "high dynamic range" refers to a range of concentrations of the target analyte, which exceeds the range of linearity for the sandwich immunoassay for the target analyte.

Figure 2:
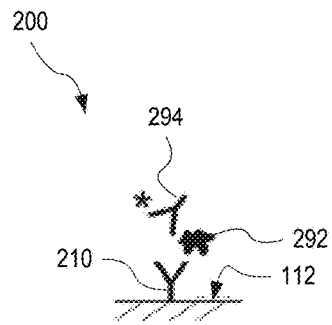
FIG. 2 illustrates an exemplary sandwich immunoassay.

FIG. 2 illustrates one exemplary sandwich immunoassay 200. Sandwich immunoassay 200 in an embodiment of the sandwich immunoassay performed in assay device 140 using sandwich immunoassay spot 122. A capture antibody 210 is immobilized to surface 112 or, alternately, to a porous material. Capture antibody 210 is an antibody for a target antigen 292 and therefore has specific affinity for binding with target antigen 292. A detect antibody 294, which is also an antibody to target antigen 292, completes sandwich immunoassay 200. Detect antibody 294 is detectable. In one example, detect antibody 294 includes a fluorescent label indicated by the star in FIG. 2. Detect antibody 294 may be the same antibody as capture antibody 210 except for further including a detectable label such as a fluorescent label.

Target antigen 292 is an embodiment of target analyte 192. Detect antibody 294 is an embodiment of detect reagent 194. A collection of capture antibodies 210 form an embodiment of sandwich immunoassay spot 122. Analysis module 150 may be configured to detect detect antibody 294.

Figure 3:
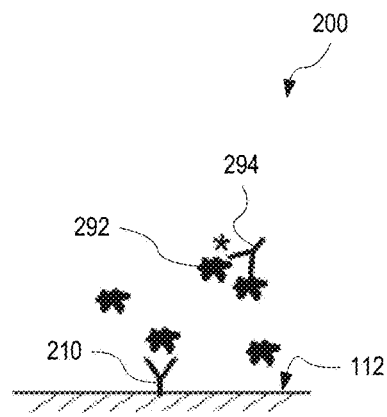
FIG. 3 illustrates the sandwich immunoassay of FIG. 2 in a scenario with an excess amount of target analyte as compared to detect reagent.

FIG. 3 illustrates sandwich immunoassay 200 in a scenario with an excess amount of target antigen 292 as compared to detect antibody 294. The excess amount of target antigen 292 causes competition between capture antibody 210 and detect antibody 294, such that not all target antigens 292 bound to capture antibody 210 succeed in also binding to a detect antibody 294. As a result, some of target antigens 292 bound to respective capture antibodies 210 lack a detect antibody 294 and therefore escape detection. This leads to the hook effect, i.e., the detected signal fails to increase in proportion to the an increase in the concentration of the target analyte.

Figure 4A:
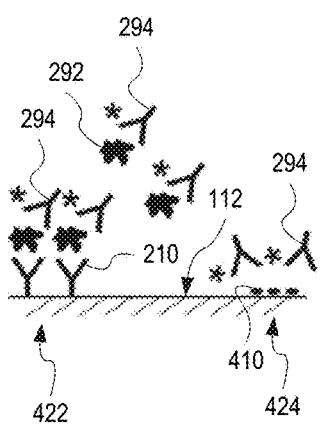
FIGS. 4A-C illustrate the sandwich immunoassay of FIG. 2 and a related exemplary competitive immunoassays in three different exemplary scenarios.
Figure 4B:
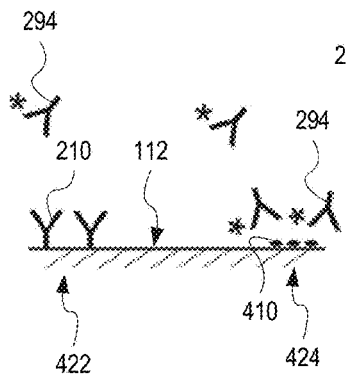
Figure 4C:
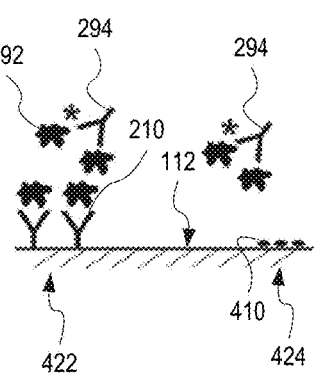

FIGS. 4A-C illustrate sandwich immunoassay 200 and a related competitive immunoassays in three different scenarios. Sandwich immunoassay 200 is performed using a sandwich immunoassay spot 422, and the competitive immunoassay is performed using a competitive immunoassay spot 424. Sandwich immunoassay spot 422 is an embodiment of sandwich immunoassay spot 122. Competitive immunoassay spot 424 is an embodiment of competitive immunoassay spot 124. FIG. 4A shows sandwich immunoassay 200 and the related competitive immunoassays in a linear range where the amount of target antigen 292 is sufficient for detection while not being so great as to cause the hook effect discussed above in reference to FIG. 3. FIG. 4B shows sandwich immunoassay 200 and the related competitive immunoassays in a scenario where the amount of target antigen 292 is insufficient for detection, or at least insufficient for accurate or reliable detection. FIG. 4C shows sandwich immunoassay 200 and the related competitive immunoassays in regime associated with the hook effect. FIGS. 4A-C are best viewed together.

Competitive assay spot 424 includes capture antigens 410 that have specific affinity for binding with detect antibody 294. In embodiments of system 100 that implement sandwich immunoassay spot 422 and competitive immunoassay spot 424 in microarray 120 of assay device 140, analysis module 150 is configured to detect antibody 294 for each of sandwich immunoassay spot 422 and competitive immunoassay spot 424.

In the scenario shown in FIG. 4A, the concentration of target antigen 292 allows for binding of detect antibody 294 to both (a) target antigen 292 bound to capture antibody 210 to complete sandwich immunoassay 200 and (b) to capture antigen 410 to complete the competitive assay. In the scenario shown in FIG. 4B, the concentration of target antigen 292 is low. This leads to a low signal for sandwich immunoassay spot 422 and a high signal for competitive immunoassay spot 424. In the scenario shown in FIG. 4C, the concentration of target antigen 292 is sufficiently high to lead to the hook effect discussed above in reference to FIG. 3. In this scenario, the signal for sandwich immunoassay spot 422 is less than it would have been in the absence of the hook effect, and the signal for competitive immunoassay spot 424 is also reduced by the excess amount of target antigen 292 at least partly preventing detect antibodies 294 from binding to capture antigens 410.

FIGS. 2, 3, and 4A-C are readily extended to a sandwich immunoassay configured to detect a target antibody as opposed to a target antigen. For example, capture antibody 210 may be replaced by a capture antigen, and capture antigen 410 may be replace by a capture antibody.

Referring again to FIG. 1, analysis module 150 measures signals 132 and 134 from sandwich immunoassay spot 122 and competitive immunoassay spot 124. Analysis module 150 measures signals 132 and 134 for the same fluidic sample 190 in the same fluidic channel 110, as opposed to, for example, (a) first measuring signal 132 for one fluidic sample 190 in fluidic channel 110 and subsequently measuring signal 134 for another (possibly identical) fluidic sample 190 in fluidic channel 110 or (b) measuring signal 132 for a fluidic sample 190 in one fluidic channel 110 and measuring signal 134 for a fluidic sample 190 in another fluidic channel 110. In one example of use, analysis module 150 measures signals 132 and 134 simultaneously or at least sufficiently close in time to avoid significant temporal evolution of a later measured one of signals 132 and 134 after measurement of a first one of signals 132 and 134.

Signal 132 is proportional to the amount of detect reagent 194 bound to sandwich immunoassay spot 122 via target analyte 192 and is indicative of the amount of target analyte 192 and detect reagent 194 available to sandwich immunoassay spot 122. Signal 134 is proportional to the amount of detect reagent 194 bound to competitive immunoassay spot 124 and is indicative of the amount of detect reagent 194 available to competitive immunoassay spot 124.

Diagram 160 plots measurement 162 by analysis module 150 of signal 132 for a range of actual concentrations of target analyte 192. In a central range 163 of relatively moderate concentrations of target analyte 192, measurement 162 is at least approximately proportional to the actual concentration of target analyte 192. This corresponds, for example, to the scenario shown in FIG. 4A. At concentrations above central range 163, corresponding for example to the scenario shown in FIG. 4C, excess amounts of target analyte 192 leads to the hook effect. At concentrations below central range 163, corresponding for example to the scenario shown in FIG. 4B, insufficient amounts of target analyte 192 leads to an inaccurate measurement 162 that fails to reflect the actual concentration of target analyte 192.

Diagram 170 plots measurement 164 by analysis module 150 of signal 134 for a range of actual concentrations of target analyte 192. In a range 165, associated with higher concentrations of target analyte 192, measurement 164 declines rapidly due to excess amounts of target analyte 192 binding up detect reagent 194 and thus preventing detection of detect antibody by analysis module 150 for competitive assay spot 124. Range 165 is associated with the hook effect. At lower concentrations, measurement 164 is less affected by the concentration of target analyte 192. However, even at the lowest concentrations, corresponding to concentrations lower than those associated with range 163, an increase in concentration of target analyte 192 leads to a slight decrease in measurement 164.

Analysis module 150 outputs the ratio of measurement 162 to measurement 164 as concentration measure 152. Without departing from the scope hereof, analysis module 150 may further process concentration measure 152. For example, analysis module 150 may apply a scaling factor universal to all concentrations of target analyte 192.

Diagram 180 plots concentration measure 152 for the same range of actual concentrations of target analyte 192 plotted in diagrams 160 and 170. Concentration measure 152 is proportional to the actual concentration of target analyte 192 over a dynamic range that exceeds the linear range 163 of diagram 160. In certain embodiments, concentration measure 152 is proportional to the actual concentration of target analyte 192 over several orders of magnitude, such as over at least four orders of magnitude. In one such embodiment, the relationship between concentration measure 152 and the actual concentration of target analyte 192 is quantitative, although nonlinear, in a range that extends beyond the range of proportionality. In this embodiment, system 100 provides a quantitative measure of the concentration of target analyte 192 over an even greater range, for example over at least six orders of magnitude.

System 100 utilizes measurement 164 of the competitive immunoassay associated with competitive immunoassay spot 124 to correct measurement 162 of the sandwich immunoassay associated with sandwich immunoassay spot 122. As a result, system 100 corrects for the hook effect at high concentrations of target analyte 192, and further corrects for non-linearity caused by insufficient concentration of target analyte 192 at low concentrations of target analyte 192. System 100 thereby performs high dynamic range immunoassays in a simple, cost-effective and rapid manner that does not require additional steps or additional fluidic circuitry. The quantity of reagents necessary to perform the immunoassays in assay device 140 is very small and in a typical embodiment of assay device 140, the cost of these reagents is only a few cents whereas the assay device itself is a few dollars. Therefore, the addition of a competitive assay spot 124 does not significantly increase the cost of the assay device 140.

System 100 is generally supplied to a use facility, such as a health care clinic or clinical diagnostics laboratory, as one analysis module 150 and a plurality of single-use embodiments of assay device 140 used to process a respective plurality of samples 190 in cooperation with analysis module. Without departing from the scope hereof, assay device 140 may be supplied as a standalone assay device, for example configured to cooperate with a third party analysis module 150. Also without departing from the scope hereof, analysis module 150 may be supplied as a standalone module configured to cooperate with third party assay devices 140.

Figure 5:
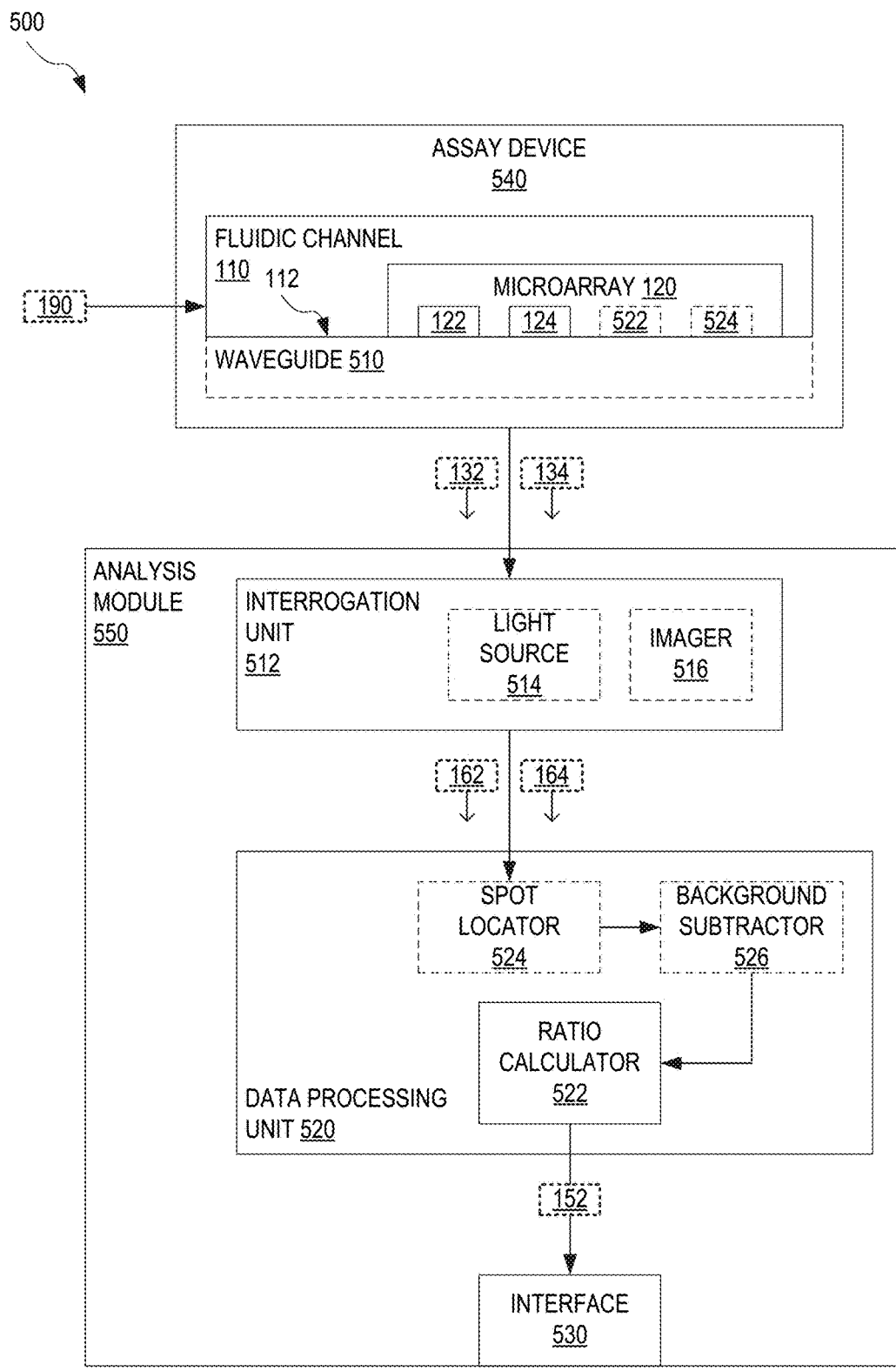
FIG. 5 illustrates another system for performing high dynamic range immunoassays, according to an embodiment.

FIG. 5 illustrates one exemplary system 500 for performing high dynamic range immunoassays. System 500 is an embodiment of system 100. System 500 includes assay device 540 and analysis module 550. Assay device 540 is an embodiment of assay device 140, and analysis module 550 is an embodiment of analysis module 150.

Assay device 540 includes fluidic channel 110 and microarray 120 disposed in fluidic channel 110. In an embodiment, fluidic channel 110 includes surface 120 formed by a surface of a waveguide 510. In this embodiment, microarray 120 is disposed on surface 112 such that microarray 120 may be evanescently illuminated by propagating in waveguide 510. Waveguide 510 is a planar waveguide, for example.

In an embodiment, microarray 120 includes at least one spot 582 of molecules configured to not bind specifically to either one or target analyte 192 and detect reagent 194. Analysis module 550 may utilize spot 582 to measure background associated with one or both of sandwich immunoassay spot 122 and competitive immunoassay spot 124. In one example, spot 582 is composed essentially of a buffer used in one or both of sandwich immunoassay spot 122 and competitive immunoassay spot 124, such that direct or indirect binding of detect reagent 194 to spot 582 is representative of non-specific binding of detect reagent 194 to one or both of sandwich immunoassay spot 122 and competitive immunoassay spot 124. Although not explicitly shown in FIG. 5 microarray 120 may include one type of spot 582 configured to provide a measure of non-specific binding of detect reagent 194 to sandwich immunoassay spot 122 and another type of spot 582 configured to provide a measure of non-specific binding of detect reagent 194 to competitive immunoassay spot 124, without departing from the scope hereof. For example, microarray 120 may include two different types of spots 582 to proper account for use of different buffers in sandwich immunoassay spot 122 and competitive immunoassay spot 124.

Optionally, microarray 120 includes at least one marker spot 584. Marker spot 584 is configured to always generate a signal that is detectable by analysis module 550. Analysis module 550 may utilize marker spot(s) 524 to locate microarray 120 and other spots within microarray 120.

Analysis module 550 includes an interrogation unit 512, a data processing unit 520, and an interface 530. Interrogation unit 512 interrogates fluidic channel 110 and is sensitive to detect reagent 194. Thus, interrogation unit 512 measures signals 132 and 134 to generate measurements 162 and 164. Interrogation unit 512 may further generate similar measurements for spots 582 and/or 584, and/or for other spots of microarray 120 not shown in FIG. 5. Interrogation unit 512 may utilize any measurement methodology, such as an electrical and/or optical measurement methodology. Analysis module 550 may use marker spot(s) 524 to ensure that interrogation unit 512 is working properly.

In one embodiment, interrogation unit 512 is based upon fluorescence imaging of signals 132 and 134 and optionally signals from other spots of microarray 120. In this embodiment, interrogation unit 512 includes a light source 514 and an imager 516. Light source 514 illuminates microarray 120 to induce fluorescence from detect reagent 194 which, in this embodiment, includes a fluorescent label. Light source 514 may be configured such that light generated by light source 514 is coupled into waveguide 510 to evanescently illuminate microarray 120. Imager 516 detects this fluorescence in a position sensitive manner. In one implementation, imager 516 is a camera that captures an image of microarray 120 showing fluorescence induced by light source 514. This image includes measurements 162 and 164, and optionally similar measurements for spots 582 and/or 584, and/or for other spots of microarray 120 not shown in FIG. 5. In another implementation, imager 516 includes a plurality of photodetectors, such as a photodiode, each positioned to measure fluorescence from a respective one of the plurality of spots in microarray 120. For example, imager 516 may include one photodetector that measures fluorescence from sandwich immunoassay spot 122 and another photodetector that measures fluorescence from competitive immunoassay spot 124.

Data processing unit 520 includes a ratio calculator 522 that calculates the ratio of measurement 162 to measurement 164 to determine concentration measure 152. Optionally, data processing unit 520 includes a background subtractor 526 that subtracts background from one or both of measurements 162 and 164 based upon measurements of signal from detect reagent 194 bound to one or more spots 582. Background subtractor 526 performs this background subtraction before calculation of concentration measure 152 by ratio calculator 522. In an embodiment, data processing unit 520 is configured to process an image of microarray 120, such as a fluorescence image. In this embodiment, data processing unit 520 may further include a spot locator 524 that, at least partly based upon identification of marker spots 584 in the image, locates other spots of microarray 120 in the image. Spot locator 524 may utilize spot location methods known in the art.

Without departing from the scope hereof, data processing unit 520 may perform further processing. In one example, data processing unit 520 performs additional background subtraction to improve the quality of concentration measure 152. In another example, data processing unit 520 averages signal measurements from a plurality of identical spots of microarray 120 to improve the quality of concentration measure 152.

Interface 530 receives concentration measure 152 from data processing unit 520 and outputs concentration measure 152 to a user or an external system.

Data processing unit 520 may be implemented as a computer that includes a processor and a non-transitory memory, wherein ratio calculator 522, and optionally one or both of spot locator 524 and background subtractor 526, are encoded in the memory as machine readable instructions that are executable by the processor.

In one implementation, analysis module 550 is a compact, self-contained instrument that accepts assay device 540. This instrument may have a footprint that is less than 450 centimeters$^2$ and weighs less than 5 kilograms. Assay device 540 may be less than 11 centimeters long, 3 centimeters wide, and 1 centimeter tall.

Without departing from the scope hereof, interrogation unit 512 may be separate from data processing unit 520 and interface 530. For example, interrogation unit 512 may be implemented in a readout instrument that is communicatively coupled to an external computation device that implements data processing unit 520 and interface 530.

System 500 is generally supplied to a use facility, such as a health care clinic or clinical diagnostics laboratory, as one analysis module 550 and a plurality of single-use embodiments of assay device 540 used to process a respective plurality of samples 190 in cooperation with analysis module. Without departing from the scope hereof, assay device 540 may be supplied as a standalone assay device, for example configured to cooperate with a third party analysis module 550. Also without departing from the scope hereof, analysis module 550 may be supplied as a standalone module configured to cooperate with third party assay devices 540 or third party assay devices 140.

Figure 6:
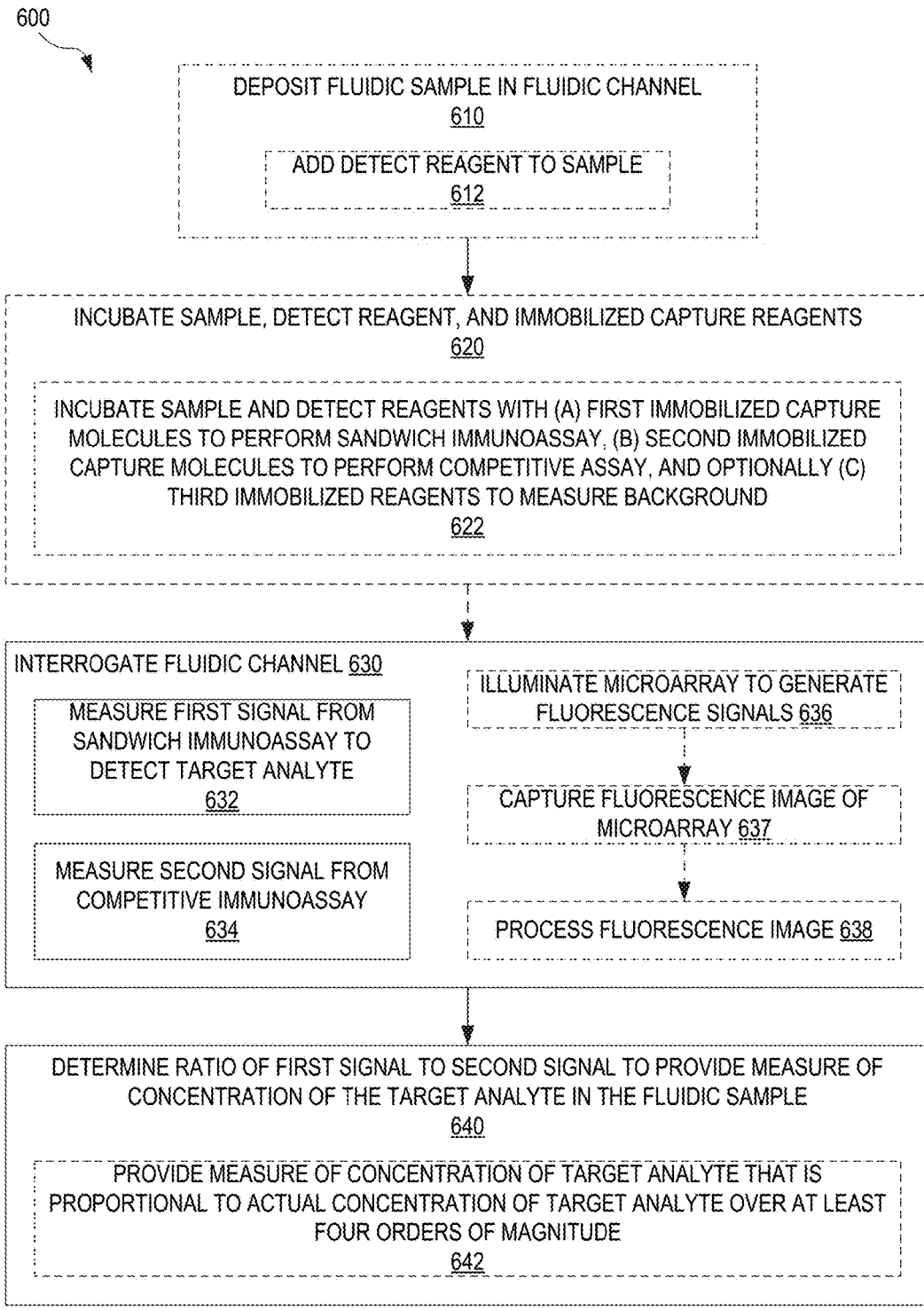
FIG. 6 illustrates a method for performing high dynamic range immunoassays, according to an embodiment.

FIG. 6 illustrates one exemplary method 600 for performing high dynamic range immunoassays. Method 600 may be performed by at least a portion of system 100, or by at least a portion of system 500.

A step 630 interrogates fluidic channel 110 with sample 190 deposited therein, wherein sample 190 includes detect reagent 194. Step 630 includes steps 632 and 634, each of which are performed for the same sample 190 in fluidic channel 110. Step 632 measures signal 132 from sandwich immunoassay spot 122 to generate measurement 162, and step 634 measures signal 134 from competitive immunoassay spot 124 to generate measurement 164. In an embodiment, method 600 performs steps 632 and 634 simultaneously or at least sufficiently close in time to avoid significant temporal evolution of a later measured signal 132 and 134 after measurement of a first one of signals 132 and 134. In one example of step 630, analysis module 150 interrogates fluidic channel 110 to measure signals 132 and 134. In another example of step 630, interrogation unit 512 interrogates fluidic channel 110 to measure signals 132 and 134.

In an embodiment, step 630 is based upon fluorescence imaging of microarray 120. In this embodiment, step 630 includes steps 636, 637, and 638. Step 636 illuminates microarray 120 to generate fluorescence signals from detect reagent 194 which, in this embodiment, is fluorescently labeled. In one example of step 636, light source 514 illuminates microarray 120. Light from light source 514 may be coupled into waveguide 510 to evanescently illuminate microarray 120. Step 637 captures a fluorescence image of microarray 120. In one example of step 637, imager 516 captures a fluorescence image of microarray 120. Step 638 processes the fluorescence image to extract measurements 162 and 164 therefrom. In one example of step 638, data processing unit 520 utilizes spot locator 524 to locate spots of microarray 120 and extract measurements of fluorescence signals from these spots. Optionally, data processing unit 520 may utilize background subtractor 526 to subtract background from one or both of sandwich immunoassay spot 122 and competitive immunoassay spot 124.

A step 640 determines concentration measure 152 by calculating the ratio of the measurement 162 to measurement 164. In one example of step 640, analysis module determines concentration measure 152 as the ratio of measurement 162 to measurement 164. In another example of step 640, ratio calculator 522 determines concentration measure 152 as the ratio of measurement 162 to measurement 164.

In certain embodiments, step 640 includes a step 642 of providing a concentration measure 152 that is proportional to the actual concentration of target analyte 192 over at least four orders of magnitude.

Steps 630 and 640 may be performed in within milliseconds or even faster such that concentration measure 152 may be, for example, output to interface 530 immediately upon completion of the immunoassays within fluidic channel 110.

Method 600 may further includes one or both of sample processing steps 610 and 620. In step 610, sample 190 is added to fluidic channel 110. In one example of step 610, a user adds sample 190 to fluidic channel 110. In another example of step 610, an instrument adds sample 190 to fluidic channel 110, for example using a pump and/or a valve. In yet another embodiment, a user and an instrument cooperate to add sample 190 to fluidic channel 110. The volume of sample 190 needed to perform the high dynamic range immunoassay need only be sufficient to fill fluidic channel at least in the region over microarray 120. This volume may be in the range between a two and fifty microliters, for example between five and twenty microliters such that a blood sample may be obtained from a finger stick. Step 610 may include a step 612 of adding detect reagent 194 to sample 190. Step 612 may be performed by a user and/or an instrument.

In step 620, sample 190 and detect reagent 194 are incubated with each other and capture molecules of microarray 120. In one example of step 620, sample 190 (including detect reagent 194) is allowed to sit in fluidic channel 110 in contact with microarray 120 for an incubation time. Step 620 includes a step 622 of incubating sample 190 and detect reagent 194 with each other and with (a) sandwich immunoassay spot 122, (b) competitive immunoassay spot 124, and optionally (c) other spots of microarray 120 such as one or both of spot(s) 522 and marker spot(s) 524. The incubation time of step 620 may be less than one hour, for example between one and twenty minutes such that the high dynamic range immunoassay may be completed rapidly. In one use scenario, sample 190 is drawn from a patient in an outpatient clinic and the high dynamic range immunoassay is completed to determine concentration measure 152 before the patient leaves the clinic. This allows for quick diagnosis and, if needed, treatment of the patient.

Figure 7A:
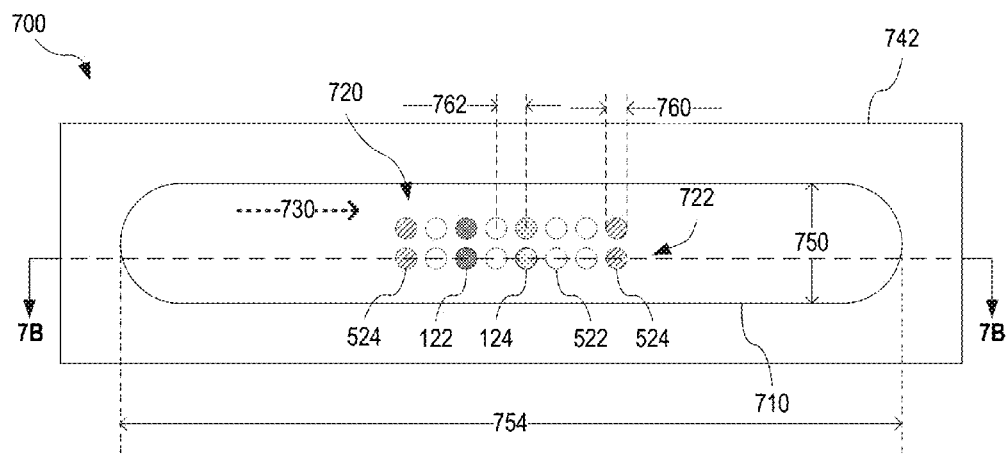
FIGS. 7A and 7B illustrate an assay device for performing high dynamic range immunoassays, according to an embodiment.
Figure 7B:
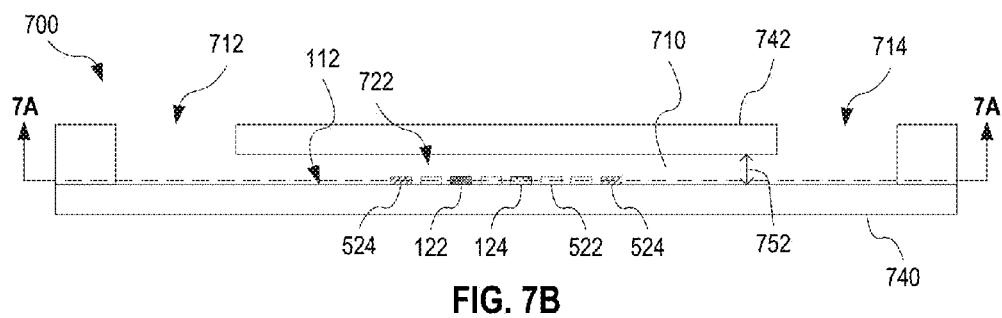

FIGS. 7A and 7B illustrate one exemplary assay device 700 for performing high dynamic range immunoassays. FIGS. 7A and 7B show assay device 700 in two orthogonal cross-sectional views. The cross sectional view in FIG. 7A is taken along line 7A-7A indicated in FIG. 7B. The cross sectional view in FIG. 7B is taken along line 7B-7B indicated in FIG. 7A. FIGS. 7A and 7B are best viewed together.

Assay device 700 is an embodiment of assay device 140 and of assay device 540. Assay device includes a substrate 740 and an upper element 742. Substrate 740 implements surface 112. Upper element 742 cooperates with substrate 740 to form a capillary channel 710. Capillary channel 710 is an embodiment of fluidic channel 110. Upper element 742 forms an inlet port 712 through which sample 190 may be added to capillary channel 710. Upper element 742 also forms an outlet port 714. In one embodiment, outlet port 714 allows for transport of sample 190 out of capillary channel 710. In another embodiment, outlet port 714 is a capillary gate that allows air to escape from capillary channel 710, so as to allow sample 190 to enter capillary channel 710 without allowing sample 190 to pass through the capillary gate. Capillary channel 710 defines a flow direction 730 for flow through capillary channel 710 from inlet port 712 towards outlet port 714.

In an embodiment, assay device 700 is a single-use or disposable assay device with substrate 740 and upper element 742 being inexpensive plastic components.

Capillary channel 710 has width 750, height 752, and length 754. In one embodiment, the volume of capillary channel 710 is less than fifty microliters or less than 20 microliters such that no more than 50 or 20 microliters, respectively, of sample 190 is needed to fill capillary channel 710 to perform a high dynamic range immunoassay therein. Width 750 may be in the range from 1 to 10 millimeters. Height 752 may be in the range from 50 microns to 2 millimeters. Length 754 may be in the range from 20 to 100 millimeters.

Capillary channel 710 includes a microarray 720 that is an embodiment of microarray 120. Microarray 720 includes at least one row 722 of spots. Row 722 is substantially parallel to flow direction 730. Row 722 includes at least one sandwich immunoassay spot 122 and at least one competitive immunoassay spot 124. Row 722 may further include one or more of (a) at least one marker spot 584 and (b) at least one spot 582 for background determination. For clarity of illustration, not all spots and rows of microarray 720 are labeled in FIGS. 7A and 7B. Each spot of microarray 720 has a diameter 760, and microarray 720 is configured with a center-to-center spacing 762 between adjacent spots. In one implementation, diameter 760 is in the range between a 0.1 and 1.0 millimeters, for example approximately 0.5 millimeters. Spacing 762 may be in the range between 0.3 and 2 millimeters, for example approximately 1 millimeter. Microarray 720 may include more of fewer spots than shown in FIGS. 7A and 7B, for example between two and one hundred spots or between two and thirty spots, as long as microarray 720 includes at least one sandwich immunoassay spot 122 and at least one competitive immunoassay spot 124.

In the embodiment shown in FIG. 7, capillary channel 710 is formed in part by surface 112 and microarray 720 is deposited on surface 112. In an alternate embodiment, microarray 720 is deposited in/on a porous material located within capillary channel 710.

In certain embodiments, substrate 740 is a planar waveguide that implements surface 112, and microarray 720 is printed onto surface 112. This planar waveguide guides light to evanescently illuminate microarray 720. The waveguide may be configured to guide light in a general propagation direction that is substantially parallel to flow direction 730, to ensure uniform illumination of all spots within each row 722.

In operation, sample 190 is added to inlet port 712 wherefrom sample 190 propagates into capillary channel 710 via capillary action. The volume of sample 190 required to perform the high dynamic range immunoassay need only be sufficient to fill capillary channel 710 from inlet port 712 to at least beyond microarray 720 and optionally to outlet port 714. In one implementation, no more than 50 or 20 microliters is needed to fill this portion of microarray 720. This is particularly useful when sample 190 is precious, such a is often the case for blood or blood products. The volume of sample 190 that interacts with microarray 720 is defined by the dimensions of capillary channel 710. Thus, an accurate determination of concentration measure 152 does not require loading an accurately metered volume of sample 190 into inlet port 712.

Figure 8:
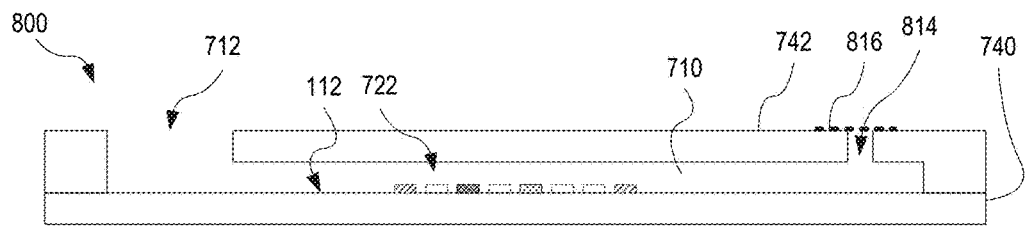
FIG. 8 illustrates another assay device for performing high dynamic range immunoassays, according to an embodiment.

FIG. 8 illustrates one exemplary assay device 800 that is an embodiment of assay device 140 and of assay device 540. FIG. 8 shows assay device 800 in the same view as used for FIG. 7B. Assay device 800 is similar to assay device 700 except that outlet port 714 is replaced by a vent 814 that forms a capillary gate. Vent 814 allows air to escape from capillary channel 710, so as to allow sample 190 to enter capillary channel 710 and fill capillary channel 710 without allowing sample 190 to pass through the vent 814.

In one embodiment, vent 814 includes a frangible seal 816 that may be punctured to open vent 814. Prior to puncture of frangible seal 816, air cannot escape capillary channel 710 through vent 814. Thus, a sample 190 added to inlet port 712 prior to puncture of frangible seal 816, cannot enter capillary channel 710. Upon puncturing frangible seal 816, sample 190 present in inlet port 712 will enter into capillary channel 710. Frangible seal 816 enables a precise start time for a high dynamic range immunoassay that is time sensitive. In one example of use, frangible seal 816 is punctured by an instrument that controls the incubation time of step 620 of method 600.

Figure 9:
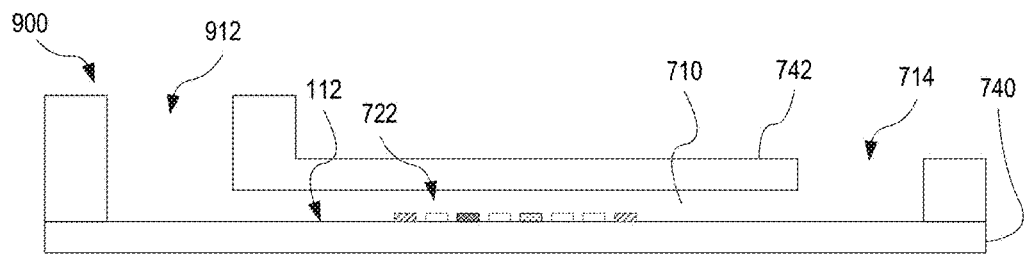
FIG. 9 illustrates yet another assay device for performing high dynamic range immunoassays, according to an embodiment.

FIG. 9 illustrates one exemplary assay device 900 that is an embodiment of assay device 140 and of assay device 540. FIG. 9 shows assay device 900 in the same view as used for FIG. 7B. Assay device 900 is similar to assay device 700 except that inlet port 712 is replaced by a taller inlet port 912 capable of holding a larger sample volume. Without departing from the scope hereof, outlet port 714 may be replaced by vent 814.

Figure 10:
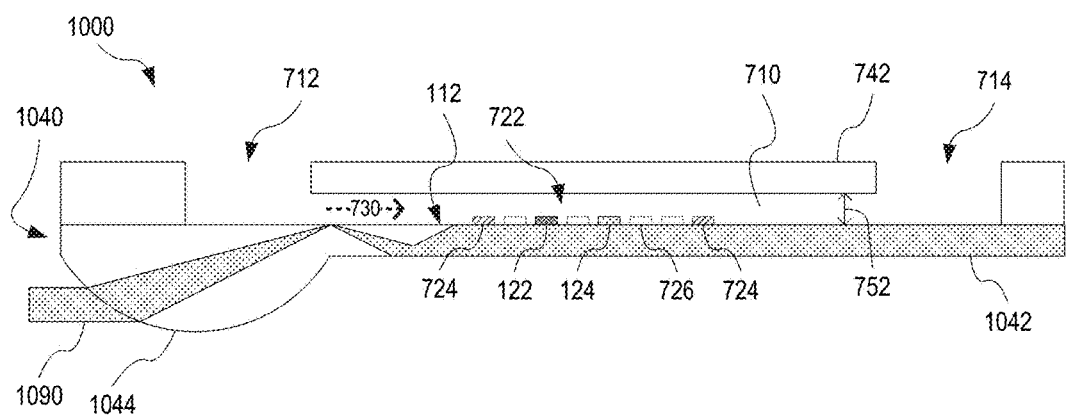
FIG. 10 illustrates a waveguide based assay device for performing high dynamic range immunoassays, according to an embodiment.

FIG. 10 illustrates one exemplary assay device 1000 that is an embodiment of assay device 140 and of assay device 540. FIG. 10 shows assay device 1000 in the same view as used for FIG. 7B. Assay device 1000 is similar to assay device 700 except for implementing substrate 740 as a planar waveguide 1040 with an integrated coupling lens 1044. Planar waveguide 1040 is an embodiment of waveguide 510. Planar waveguide 1040 includes a planar waveguiding portion 1042 and coupling lens 1044. Coupling lens 1044 receives a light beam 1090, for example generated by light source 514, and couples light beam 1090 into planar waveguiding portion 1042 to evanescently illuminate microarray 720. The propagation direction of light within waveguiding portion 1042 is substantially parallel to flow direction 730. This helps ensure uniform illumination of all spots within each row 722.

Without departing from the scope hereof, inlet port 712 may be replaced by inlet port 912 and outlet port 714 may be replaced by vent 814.

EXAMPLE 1

Measurement of Ebola VP40 Antigen Concentration

In this example, an embodiment of system 500 was used to measure the concentration of the Ebola VP40 antigen using assay device 1000 implementing vent 814. This example is performed according to an embodiment of method 600. The example uses embodiments of light source 514 and imager 516 to perform fluorescence imaging of a microarray in assay device 1000. The example further uses embodiments of spot locator 524 and background subtractor 526 to processes the fluorescence images and data extracted therefrom.

Figures 11, 12, 13:
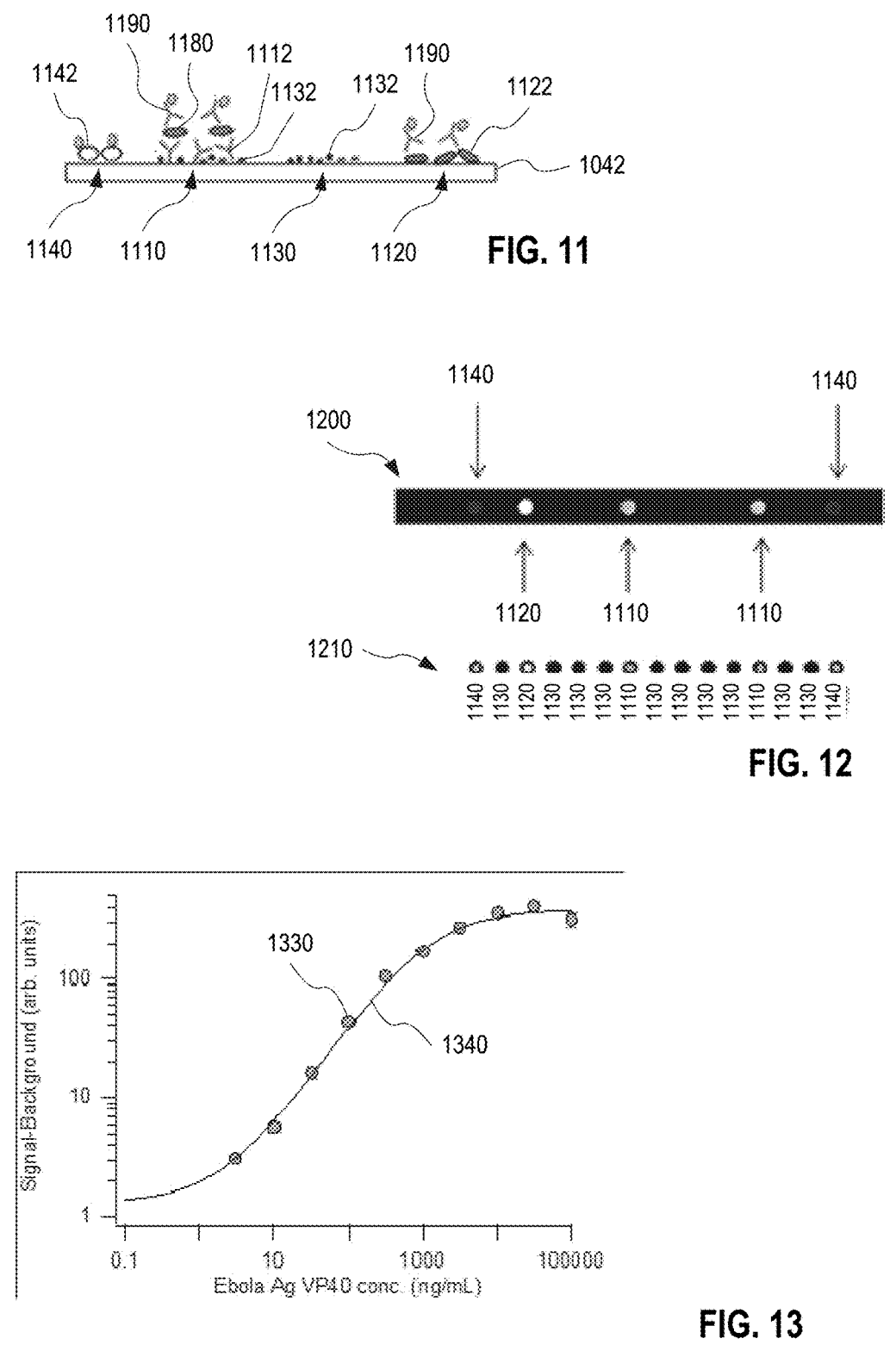

FIG. 11 schematically illustrates the high dynamic range immunoassay of Example 1. This assay utilizes four types of spots: (a) a sandwich immunoassay spot 1110 that is an embodiment of sandwich immunoassay spot 122, (b) a competitive immunoassay spot 1120 that is an embodiment of competitive immunoassay spot 124, (c) a print buffer spot 1130 that is an embodiment of spot 582, and (d) a marker spot 1140 that is an embodiment of marker spot 584.

Marker spot 1140 includes fluorescently labeled protein and is used to align the imaging software, implemented by spot locator 524 and demonstrate that the reagents are reactive and that interrogation unit 512 is operating.

Sandwich immunoassay spot 1110 includes Zaire anti-Ebola pAb capture antibodies 1112 to forms the sandwich immunoassay with the Ebola VP40 antigen 1180. Ebola VP40 antigen 1180 is an example of target analyte 192. Capture antibody 1112 binds to the Ebola VP40 antigen 1180 and the dye conjugated pAb 1190, an example of detect reagent 194, binds to the Ebola VP40 antigen 1180 and fluoresces when illuminated. Print buffer spot 1130 is printed next to sandwich immunoassay spot 1110 and is not labeled with any fluorophores. Print buffer spot 1130 is used for background subtraction, by background subtractor 526 to improve the assay sensitivity and accuracy. Competitive immunoassay spot 1120 is used in the competitive antigen immunoassay where dye conjugated pAb 1190 competes with Ebola VP40 antigen 1180 in the sample for binding sites. Competitive immunoassay spot 1120 includes aZaire VP40 antibody.

FIG. 12 shows a fluorescence image of the microarray 1200 used in this example. Microarray 1200 is an example of microarray 720 implementing a single row 722. The fluorescence image was captured by imager 516 upon evanescent illumination of microarray 1200 via waveguide 1040. Microarray 1200 is printed with nanoliters of liquid reagent, which dries on the surface of waveguide 1040. Since such a small quantity of reagent is used, these microarrays are very cost-effective. Microarray 1200 included with 15 reagent spots. Layout diagram 1210 shows a schematic representation of spots of microarray 1200 and their reagent content. The two print buffer spots 1140 at the ends of microarray 1200 were printed with fluorophore labeled bovine serum albumin and provide a control that the instrument and fluorophore are operating. Furthermore, these spots function as fiducials that are used in image processing, by spot locator 524, to detect the array location in the fluorescence image. Microarray 1200 includes two sandwich immunoassay spots 1110, one competitive assay spot 1120, and ten print buffer spots 1130. Not all ten print buffer spots 1130 are necessary and at least some of these spots could be used for a different immunoassay, if desired.

In this example, anti-Ebola pAb was used as both a capture and a detect antibody in the sandwich assay format. The detect reagent, dye conjugated pAb 1190, was conjugated with a fluorescent dye Alexa Fluor® 647 (Life Technologies).

To prepare the sample (an example of sample 190) for detection, 25 microliters of sample was combined in a microtube with 10 microliters of dye-conjugated anti-Ebola pAb 1190 in diluent and mixed. Approximately 30 microliters of this mixture was transferred to the inlet port of the cartridge in step 610, which was then incubated in step 620 before measurement in step 630. The measurement in step 630 was performed by coupling light from a diode laser at 639 nm into the waveguide in step 636. Fluorescence from the dye labeled antibody was imaged in step 637. The intensity of each spot on the microarray was extracted from the image in step 638. FIG. 12 shows an such an exemplary fluorescence image.

FIG. 13 shows a standard curve 1340 of the sandwich immunoassay associated with sandwich immunoassay spot 1110. Standard curve 1340 is generated from actual measurements 1330 (examples of measurements 162) of signal from sandwich immunoassay spots 1110, with background subtraction in step 638 based upon print buffer spots 1130. The linear range of standard curve 1340 is limited by the hook effect. The linear range is from VP40 Ag concentrations of approximately 2 ng/mL to approximately 2 µg/mL, which spans three orders of magnitude. This dynamic range is not sufficient for the range of sample concentrations that is expected to be tested.

Figures 14, 15:
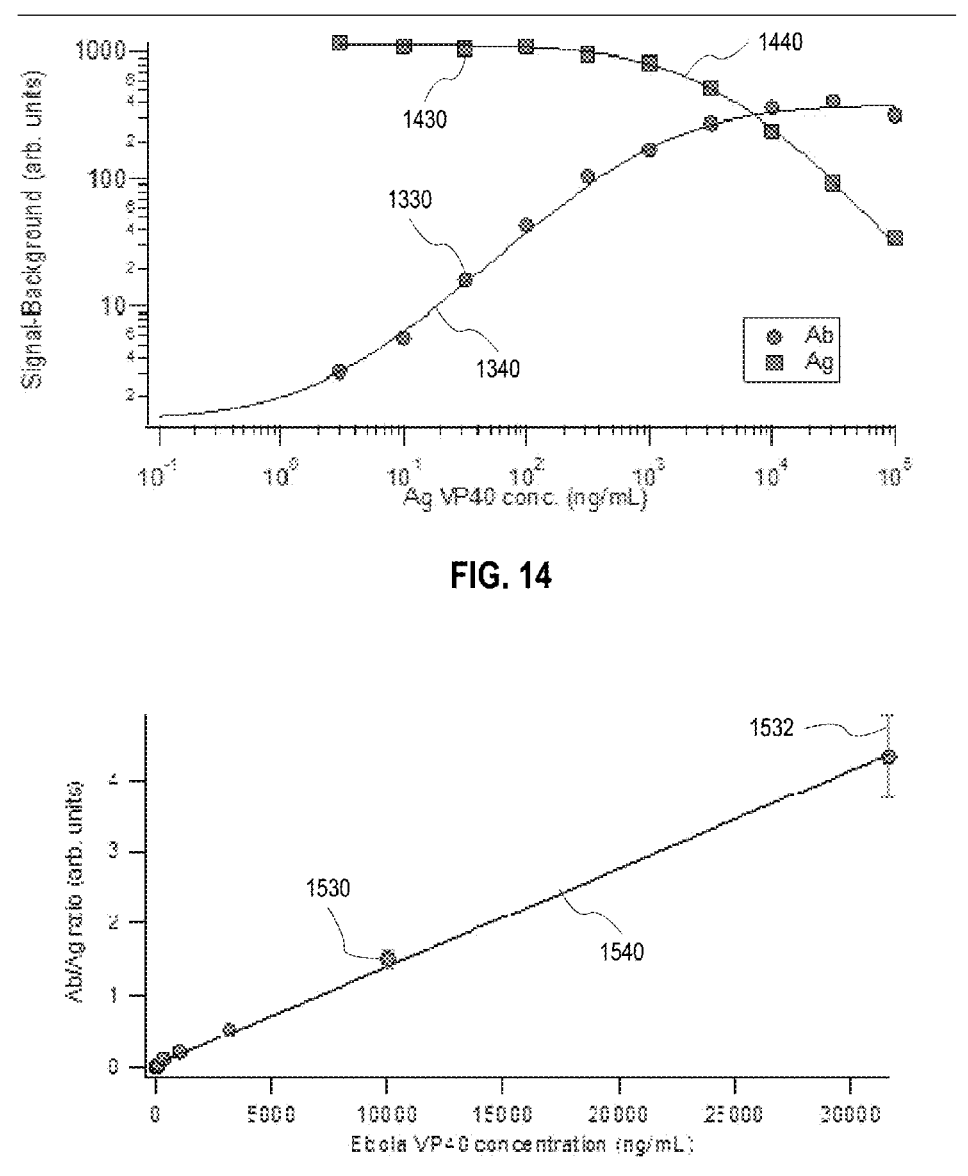

FIG. 14 shows standard curve 1340 for the sandwich immunoassay together with a standard curve 1440 for the competitive immunoassay associated with competitive immunoassay spot 1120. Standard curve 1440 is based upon measurements 1430 (examples of measurements 164) of competitive immunoassay spots 1120, with background subtraction in step 638 based upon print buffer spots 1130. Over this range of sample concentrations, the competitive antigen assay also exhibits a linear decrease in intensity as is expected. At higher antigen concentrations, both the sandwich immunoassay and the competitive antigen immunoassay exhibit non-linearities due to the hook effect.

FIG. 15 shows the ratio 1530 of sandwich immunoassay measurements 1330 to competitive immunoassay measurements 1430. Ratio 1530 is an example of concentration measure 152. Error bars 1532 indicate +/− one standard deviation. A straight line 1540 is fitted to ratio 1530. Although both the sandwich immunoassay and the competitive immunoassay individually suffer from non-linearities at high sample concentrations, as evident in FIG. 14, the ratio 1530 of the fluorescence intensities measured from these immunoassays is very well-behaved and is linear over a range of 2 ng/mL to 32 µg/mL. The linear range spans more than four orders of magnitude. The quantitative range of this assay is even larger extending up to concentrations of 100 µg/mL, spanning more than 4.5 orders of magnitude. The large linear and quantitative ranges allow for the measurement of all expected concentrations of antigen.

Combinations of Features

Features described above as well as those claimed below may be combined in various ways without departing from the scope hereof. For example, it will be appreciated that aspects of one system, method, or device for performing a high dynamic range immunoassay described herein may incorporate or swap features of another system, method, or device for performing a high dynamic range immunoassay described herein. The following examples illustrate possible, non-limiting combinations of embodiments described above. It should be clear that many other changes and modifications may be made to the systems, methods, and devices described herein without departing from the spirit and scope of this invention:

(A1) A method for performing a high dynamic range immunoassay may include (a) measuring a first signal from a sandwich immunoassay to detect a target analyte in a fluidic sample in a fluidic channel and a second signal from a competitive immunoassay associated with the target analyte in the same fluidic sample in the fluidic channel, and (b) determining the ratio of the first signal to the second signal to provide a measure of the concentration of the target analyte in the fluidic sample.

(A2) In the method denoted as (A1), the measure may be applicable to a high dynamic range of concentrations of the target analyte.

(A3) In either of both of the methods denoted as (A1) and (A2), the first signal may be indicative of amount of the target analyte and associated detect reagent available to the sandwich immunoassay, and the second signal may be indicative to the amount of the associated detect reagent available to the sandwich immunoassay.

(A4) In any of the methods denoted as (A1) through (A3), in the step of measuring, the first signal may be proportional to the amount of the target analyte detected in the sandwich immunoassay via a detect reagent, and the second signal may be proportional to the amount of the detect reagent being detected in the competitive assay.

(A5) In the method denoted as (A4), the step of measuring may include (a) measuring the first signal as a fluorescence signal from the detect reagent, the detect reagent being fluorescently labeled, and (b) measuring the second signal as a fluorescence signal from the detect reagent.

(A6) In either of both of the methods denoted as (A4) and (A5), the step of measuring may include (a) measuring the first signal as signal from a detect reagent of a surface-based sandwich immunoassay that uses first capture molecules immobilized to a surface of the fluidic channel, the detect reagent being bound to the first capture molecules via the target analyte, and (b) measuring the second signal as signal from the detect reagent of a surface-based competitive immunoassay between second capture molecules immobilized to the surface and the detect reagent, the detect reagent being bound directly to the second capture molecules in the competitive assay.

(A7) In the method denoted as (A6), the target analyte may be a first antigen, the first capture molecules may be first antibodies to the first antigen, the detect reagent may be second antibodies to the first antigen, and the second capture molecules may be second antigens to the second antibodies.

(A8) In the method denoted as (A7), the second antibodies may be fluorescently labeled versions of the first antibodies.

(A9) Any of the methods denoted as (A6) through (A8) may include (a) in the step of measuring the first signal, measuring signal from a first spot including the first capture molecules, and (b) in the step of measuring the second signal, measuring signal from a second spot including the second capture molecules.

(A10) In the method denoted as (A9), each of the first signal and the second signal may be a fluorescence signal, and the step of measuring may include capturing a fluorescence image of the surface and processing the fluorescence image to determine the first signal and the second signal.

(A11) Either or both of the methods denoted as (A9) and (A10) may further include (a) in the step of measuring, measuring a background signal from a third spot including third molecules immobilized to the surface, and (b) prior to the step of determining, subtracting the background signal from each of the first signal and the second signal to remove background contribution.

(A12) Any of the methods denoted as (A1) through (A11) may further include, prior to the step of measuring, (a) depositing the sample in the fluidic channel, and (b) simultaneously incubating the sample with reagents of both the sandwich immunoassay and the competitive immunoassay.

(A13) In the method denoted as (A12), the step of simultaneously incubating may include (a) incubating the sample with a detect reagent common to the sandwich immunoassay and the competitive assay, and (b) incubating the sample and the detect reagent with (i) a first spot including first capture molecules immobilized to a surface of the fluidic channel to perform the sandwich immunoassay and (ii) a second spot including second capture molecules immobilized to the surface to perform the competitive assay.

(A14) In any of the methods denoted as (A1) through (A13), the step of determining may include providing a measure of the concentration of the target analyte that is proportional to actual concentration of the target analyte in the fluidic sample over at least four orders of magnitude of the actual concentration.

(B1) A device for performing an assay on a sample may include a capillary channel for containing the sample, and a microarray immobilized to a surface of the capillary channel, wherein the microarray includes (a) a first spot including a first capture molecule for specifically binding to a target analyte in the sample to perform a sandwich immunoassay involving the first capture molecule, the target analyte, and a detect reagent added to the sample, and (b) a second spot including a second capture molecule for specifically binding to the detect reagent to perform a competitive assay with the detect reagent to measure amount of detect reagent available to the sandwich immunoassay.

(B2) In the device denoted as (B1), the sandwich immunoassay and the competitive assay may cooperate to provide a measure of concentration of the target analyte applicable to a high dynamic range of concentrations of the target analyte.

(B3) In either or both of the devices denoted as (B1) and (B2), the microarray may further include at least one third spot that includes a third capture molecule for measuring background, wherein the third capture molecule is configured to not bind specifically to either of the target analyte and the detect reagent.

(B4) In any of the devices denoted as (B1) through (B3), the surface may be a surface of a planar waveguide for guiding light to evanescently illuminate the microarray to read out (a) a first fluorescence signal from the first sandwich immunoassay indicative of amount of and a second fluorescence signal from the competitive assay, (B5) In any of the devices denoted as (B1) through (B4), the capillary channel may further include an inlet port for receiving the sample upstream of the microarray, and an outlet port downstream from the microarray, wherein the capillary channel defines a direction of flow of the sample from an inlet port to an outlet port of the fluidic channel, and wherein the first spot and the second spot are placed in a row of the microarray parallel to the direction of flow.

(B6) In the device denoted as (B5), the row may further include a third spot including a third molecule for measuring a background contribution to each of the first fluorescence signal and the second fluorescence signal, the third molecule being configured to not bind specifically to either of the target analyte and the detect reagent.

(B7) In any of the devices denoted as (B1) through (B6), the surface may be a surface of a planar waveguide for guiding light to evanescently illuminate the microarray to read out (a) a first fluorescence signal from the first sandwich immunoassay indicative of amount of and a second fluorescence signal from the competitive assay.

(B8) In the device denoted as (B7), the planar waveguide may be configured to guide light along the direction of flow of sample through the capillary channel to ensure equal evanescent illumination of the first spot and the second spot.

(B9) In any of the devices denoted as (B1) through (B8), the target analyte may be a first antigen, the detect reagent may be an antibody with specific affinity for binding with the target analyte, the first capture molecule may be a first antibody with specific affinity for binding with the target analyte, and the second capture molecule may be a second antigen with specific affinity for binding with the detect reagent.

Changes may be made in the above systems, methods, and devices without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present compositions, devices, and methods, which, as a matter of language, might be said to fall therebetween.

What is claimed is:

1. A system for performing an assay on a sample, comprising:
   an assay device including:
      a capillary channel for containing the sample, and
      a microarray immobilized to a surface of the capillary channel, the microarray including (a) a first spot including a first capture molecule for specifically binding to a target analyte in the sample as part of a sandwich immunoassay involving the first capture molecule, the target analyte, and a detect reagent in the sample, and (b) a second spot including a second capture molecule for specifically binding to the detect reagent in a competitive assay; and
   an analysis module including:
      an interrogation unit for measuring a first signal from the first spot and a second signal from the second spot,
      a ratio calculator for calculating a ratio of the first signal to the second signal, as measured or after background subtraction, the ratio being proportional to concentration of the target analyte for a high dynamic range of concentrations of the target analyte, and
      an interface for outputting the ratio as a measure of the concentration.

2. The system of claim 1, the microarray further comprising at least one third spot including a third capture molecule for measuring background.

3. The system of claim 1, the surface being a surface of a planar waveguide for guiding light to evanescently illuminate the microarray to read out a first fluorescence signal from the first sandwich immunoassay and a second fluorescence signal from the competitive assay.

4. The system of claim 1,
   the capillary channel further comprising:
      an inlet port for receiving the sample upstream of the microarray, and
      an outlet port downstream from the microarray;
   the capillary channel defining a direction of flow of the sample from an inlet port to an outlet port of the fluidic channel; and
   the first spot and the second spot being placed in a row of the microarray parallel to the direction of flow.

5. The system of claim 4, the surface being a surface of a planar waveguide for guiding light to evanescently illuminate the microarray, with equal evanescent illumination for the first spot and the second spot, to read out (a) a first fluorescence signal from the sandwich immunoassay and (b) a second fluorescence signal from the competitive assay.

6. The system of claim 5, the row further comprising a third spot including a third molecule for measuring a background contribution to each of the first fluorescence signal and the second fluorescence signal.

7. The system of claim 1, the target analyte being a first antigen, the detect reagent being an antibody with specific affinity for binding with the target analyte, the first capture molecule being a first antibody with specific affinity for binding with the target analyte, and the second capture molecule being a second antigen with specific affinity for binding with the detect reagent.

8. The system of claim 1, the high dynamic range exceeding range of proportionality between the first signal and the concentration.

9. The system of claim 1, the high dynamic range being at least four orders of magnitude.

* * * * *